United States Patent
Gladnick (10) Patent No.: US 9,304,089 B2
(45) Date of Patent: Apr. 5, 2016

(54) SYSTEM AND METHOD FOR OBTAINING IMAGES WITH OFFSET UTILIZED FOR ENHANCED EDGE RESOLUTION

(71) Applicant: Mitutoyo Corporation, Kawasaki-Shi (JP)

(72) Inventor: Paul Gerard Gladnick, Seattle, WA (US)

(73) Assignee: Mitutoyo Corporation, Kanagawa-ken (JP)

( * ) Notice: Subject to any disclaimer, the term of this patent is extended or adjusted under 35 U.S.C. 154(b) by 574 days.

(21) Appl. No.: 13/857,319

(22) Filed: Apr. 5, 2013

(65) Prior Publication Data

US 2014/0300726 A1  Oct. 9, 2014

(51) Int. Cl.
*G06K 9/00* (2006.01)
*G01N 21/88* (2006.01)
*G06T 3/40* (2006.01)
*G01B 11/02* (2006.01)

(52) U.S. Cl.
CPC ............ *G01N 21/8803* (2013.01); *G01B 11/02* (2013.01); *G01N 21/8851* (2013.01); *G06T 3/4069* (2013.01); *G01B 2210/52* (2013.01)

(58) Field of Classification Search
USPC .................. 382/141, 145, 147, 149, 199, 298
See application file for complete search history.

(56) References Cited

U.S. PATENT DOCUMENTS

| | | | |
|---|---|---|---|
| 5,335,091 A | 8/1994 | Palum | |
| 5,811,754 A * | 9/1998 | Nakatani | B23K 26/04 219/121.7 |
| 6,542,180 B1 | 4/2003 | Wasserman et al. | |
| 7,061,524 B2 | 6/2006 | Liu et al. | |
| 7,064,779 B1 | 6/2006 | Pine | |
| 7,084,910 B2 | 8/2006 | Amerson et al. | |
| 7,324,682 B2 | 1/2008 | Wasserman | |
| 7,409,653 B2 | 8/2008 | Sengupta et al. | |
| 7,420,592 B2 * | 9/2008 | Freeman | H04N 3/1587 348/219.1 |
| 7,454,053 B2 | 11/2008 | Bryll et al. | |
| 7,499,584 B2 | 3/2009 | Delaney | |
| 7,567,713 B2 | 7/2009 | Ding | |
| 7,778,493 B2 | 8/2010 | Ho et al. | |
| 8,111,905 B2 | 2/2012 | Campbell | |
| 8,111,938 B2 | 2/2012 | Bryll et al. | |

(Continued)

OTHER PUBLICATIONS

"QVPak 3D CNC Vision Measuring Machine User's Guide," published Jan. 2003, 330 pages.

(Continued)

*Primary Examiner* — John Strege
(74) *Attorney, Agent, or Firm* — Seed IP Law Group PLLC (57) ABSTRACT

A method in a machine vision inspection system for obtaining two images of a workpiece with a desired sub-pixel offset between the images. The images are acquired using a fast multiple image acquisition mode of operation of a camera in the machine vision inspection system. In various implementations, the method includes removing the offset between the images such that the workpiece is congruent in the images and combining the congruent image data. The combined image data has a resolution better than that allowed by the native resolution of a camera that acquires images in the machine vision inspection system. The method may be implemented in an edge feature video tool for measuring edge features on the workpiece. The motion direction utilized for obtaining the two images may be made to be transverse to the edge direction of an edge that is being measured.

32 Claims, 8 Drawing Sheets

(56) References Cited

U.S. PATENT DOCUMENTS

| | | |
|---|---|---|
| 8,130,278 B2 | 3/2012 | Border et al. |
| 8,135,234 B2 | 3/2012 | Tourapis et al. |
| 2005/0206885 A1* | 9/2005 | Kurata .............. G01N 21/9501 356/237.2 |
| 2005/0280714 A1* | 12/2005 | Freeman .............. H04N 3/1587 348/219.1 |
| 2007/0058966 A1* | 3/2007 | Irinouchi ........... H04N 5/23248 396/153 |
| 2007/0268388 A1* | 11/2007 | Watanabe ............. H04N 3/155 348/294 |
| 2012/0274811 A1* | 11/2012 | Bakin ................. H04N 3/1593 348/239 |

OTHER PUBLICATIONS

"QVPAK 3D CNC Vision Measuring Machine Operation Guide," published Sep. 1996, 86 pages.

Wikipedia—the free encyclopedia, "Particle Image Velocimetry," http://en.wikipedia.org/wiki/Particle_image_velocimetry, downloaded on Mar. 20, 2013, pp. 1-12.

\* cited by examiner

| PT | Tube EFL (mm) | Overall M | Optical resolution (μm) [ ½ Airy d ] | Projected ½ blur size (μm) | Required pixel size (μm) |
|---|---|---|---|---|---|
| 1X | 100 | 5 | 0.65 | 3.25 | 1.63 |
| 2X | 200 | 10 | | 6.5 | 3.25 |
| 4X | 400 | 20 | | 13 | 6.5 |

SYSTEM AND METHOD FOR OBTAINING IMAGES WITH OFFSET UTILIZED FOR ENHANCED EDGE RESOLUTION

BACKGROUND

Precision machine vision inspection systems (or "vision systems" for short) can be utilized to obtain precise dimensional measurements of inspected objects and to inspect various other object characteristics. Such systems may include a computer, a camera and optical system, and a precision stage that is movable in multiple directions so as to allow the camera to scan the features of a workpiece that is being inspected. One exemplary prior art system that is commercially available is the QUICK VISION® series of PC-based vision systems and QVPAK® software available from Mitutoyo America Corporation (MAC), located in Aurora, Ill. The features and operation of the QUICK VISION® series of vision systems and the QVPAK® software are generally described, for example, in the QVPAK 3D CNC Vision Measuring Machine User's Guide, published January 2003, and the QVPAK 3D CNC Vision Measuring Machine Operation Guide, published September 1996, each of which is hereby incorporated by reference in their entirety. This product, as exemplified by the QV-302 Pro model, for example, is able to use a microscope-type optical system to provide images of a workpiece at various magnifications, and move the stage as necessary to traverse the workpiece surface beyond the limits of any single video image. A single video image typically encompasses only a portion of the workpiece being observed or inspected, given the desired magnification, measurement resolution, and physical size limitations of such systems.

Image acquisition may be performed while using relative motion between the camera and the workpiece stage, thereby significantly increasing inspection throughput. It is advantageous for such systems to include strobe lighting illumination to assist with the acquisition of images during continuous motion without smearing (or blurring) the image. One exemplary method for acquiring images using continuous motion operations that can be used on different machine vision systems is described in U.S. Pat. No. 7,499,584, which is hereby incorporated by reference in its entirety.

General purpose precision machine vision inspection systems, such as the QUICK VISION™ system, are also generally programmable to provide automated video inspection. U.S. Pat. No. 6,542,180 (the '180 patent) teaches various aspects of such automated video inspection and is incorporated herein by reference in its entirety. As taught in the '180 patent, automated video inspection metrology instruments generally have a programming capability that allows an automatic inspection event sequence to be defined by the user for each particular workpiece configuration. This can be implemented by text-based programming, for example, or through a recording mode which progressively "learns" the inspection event sequence by storing a sequence of machine control instructions corresponding to a sequence of inspection operations performed by a user with the aid of a graphical user interface, or through a combination of both methods. Such a recording mode is often referred to as "learn mode" or "training mode" or "record mode." Once the inspection event sequence is defined in "learn mode," such a sequence can then be used to automatically acquire (and additionally analyze or inspect) images of a workpiece during "run mode."

The machine control instructions including the specific inspection event sequence (i.e., how to acquire each image and how to analyze/inspect each acquired image) are generally stored as a "part program" or "workpiece program" that is specific to the particular workpiece configuration. For example, a part program defines how to acquire each image, such as how to position the camera relative to the workpiece, at what lighting level, at what magnification level, etc. Further, the part program defines how to analyze/inspect an acquired image, for example, by using one or more video tools such as edge/boundary detection video tools.

Video tools (or "tools" for short) and other graphical user interface features may be used manually to accomplish manual inspection and/or machine control operations (in "manual mode"). Their set-up parameters and operation can also be recorded during learn mode, in order to create automatic inspection programs, or "part programs". Video tools may include, for example, edge/boundary detection tools, autofocus tools, shape or pattern matching tools, dimension measuring tools, and the like.

Part programs for acquiring images of edge features typically specify a level of magnification. When selecting a level of magnification, various tradeoffs may be considered. For example, higher levels of magnification may provide higher resolution, but also have a smaller field of view with respect to the overall workpiece and may result in greater distortion, in addition to requiring more expensive hardware for the magnifying elements. Lower levels of magnification may provide a larger field of view and less distortion, as well as lower cost, but may not provide the desired level of resolution and corresponding accuracy for certain applications. In some such cases, the resolution of an image of an object is limited by the pixel spacing in the camera detector, in that the spatial sampling on the object is determined by the pixel spacing and the magnification. A method is known to address this situation by acquiring a plurality of images that are stepped or offset by a known sub-pixel increment relative to one another, and the multiple sets of image data are then combined to effectively increase the image sampling density on the object. However, in some cases such methods have been too complicated to be understood and implemented by relatively unskilled users, or too slow to be practical in many industrial environments and/or applications. Some prior art systems have proposed a dithering motion of the camera or an optical component in order to provide the desired offset "automatically". However, such methods are mechanically complicated, and may introduce vibrations and/or non-repeatability that are incompatible with precision inspection tolerances. An improved method and system that allows a desired level of resolution and accuracy to be obtained by relatively unskilled users, while utilizing relatively less expensive systems (e.g. existing systems) and lower levels of magnification would be desirable.

DETAILED DESCRIPTION

A method for acquiring a plurality of images having sub-pixel offsets relative to one another in a machine vision inspection system is provided. The machine vision inspection system includes an optical system which provides a magnification M, and a camera which includes a first pixel pitch P and a fast multiple image acquisition mode of operation. Sub-pixel offset image sampling operations are utilized which include providing a first image acquisition motion and acquiring a plurality of images of a region of interest. The first image acquisition motion includes moving one of the workpiece and the camera relative to one another at a first speed S along a first direction. The plurality of images are acquired during the image acquisition motion using the fast multiple image acquisition mode of operation of the camera. The plurality of images include at least a first image of the region of interest acquired at a first time t1, and a second image of the region of interest acquired at a second time t2 after the first time t1. An offset O between the first and second images relative to objects in their field of view (FOV) is approximately equal to $M*S*(t2-t1)$ and the machine vision inspection system is configured such that O does not equal nP, where n is an integer. In various implementations, the offset O may fall within a range of $(n+0.2)P<O<(n+0.8)P$. The fast multiple image acquisition mode of operation of the camera system operates such that the difference between the first and second times $(t2-t1)$ may be at most 50 microseconds, or at most 25, 10 or 5 microseconds in various embodiments, or even less if allowed by the camera system.

In various implementations, the first pixel pitch P may include at least one of a column-direction pixel pitch Py or a row-direction pixel pitch Px. The offset O may comprise a component Ox along a column direction of the camera having the pixel pitch Px and a component Oy along a row direction of the camera having the pixel pitch Py. The first image acquisition motion and an image timing in the fast multiple image acquisition mode of operation may be configured such that at least one of the offset components comprises a non integer number K times the corresponding pixel pitch. In one implementation, the non integer number K falls within a range of $(n+0.2)<K<(n+0.8)$, where n is an integer.

The method may further include removing or compensating for the offset O such that the workpiece is congruent in the images and/or image data. The congruent image data may then be combined to provide image data that has a resolution better than that allowed by the native resolution of a camera that acquires images in the machine vision inspection system. The combining of the congruent image data may be based on at least one of position latching data, correlation analysis of the images, or motion and timing data.

In various implementations, the operations may be included in a multiple image mode of an edge tool. The edge tool may include a single image mode and a multiple image mode, the multiple image mode being utilized based on at least one of a magnification and a user selection. The image data from the first and second images taken during the multiple image mode may be combined to increase the resolution to a desired level. A composite image that is utilized for determining the edge location may be made based on the combined data of the first and second images. The composite image may be displayed during a learn mode. The system parameters used during the multiple image mode to provide the increased resolution image data may be configured during the learn mode, and the configuration may be recorded in a part program.

The first image acquisition motion may be made in a direction that is transverse to an edge direction of an edge that is being measured. In some embodiments and/or applications, a learn mode may include performing and/or defining operations such as operations for measuring the edge, determining an angle of the edge, setting the motion direction transverse to the edge (e.g. to an angle equal to the angle of the edge plus approximately 90 degrees, in one embodiment), computing two waypoints based on the motion direction and tool location parameters, and the like. In certain instances, the first and second images may include a plurality of edges of the workpiece in the region of interest. In such cases, if a determination is made that a plurality of edge tools are being utilized within the region of interest with respect to the plurality of edges, then the learn mode may utilize a multi-edge tool routine. The multi-edge tool routine may include determining the angles of the plurality of edges, determining if a single motion direction can be determined that is within a specified range of degrees from perpendicular with respect to each of the angles of the plurality of edges, and if so, using the determined motion direction, and if not, adding at least a second motion direction for obtaining at least a third image. The learn mode may also provide an option to a user to assist with the determination of the motion direction.

Various embodiments of the invention are described below. The following description provides specific details for a thorough understanding and an enabling description of these embodiments. One skilled in the art will understand, however, that the invention may be practiced without many of these details. In addition, some well-known structures or functions may not be shown or described in detail, so as to avoid unnecessarily obscuring the relevant description of the various embodiments. The terminology used in the description presented below is intended to be interpreted in its broadest reasonable manner, even though it is being used in conjunction with a detailed description of certain specific embodiments of the invention.

Figure 1:
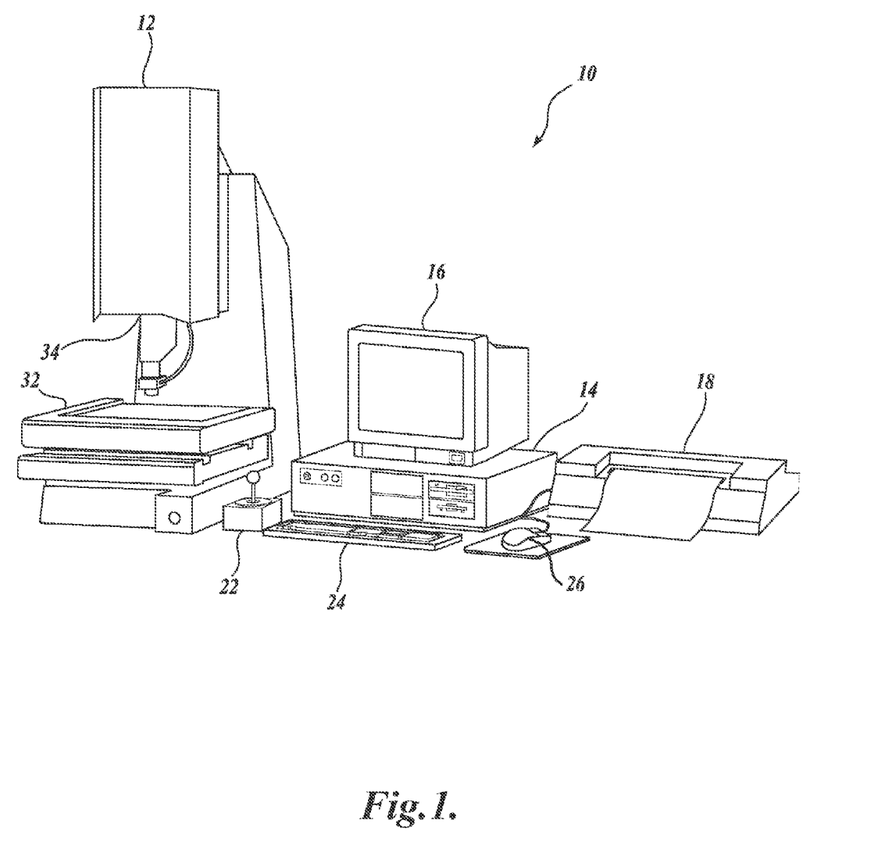
FIG. 1 is a diagram showing various typical components of a general purpose precision machine vision inspection system.

FIG. 1 is a block diagram of one exemplary machine vision inspection system 10 usable in accordance with methods described herein. The machine vision inspection system 10 includes a vision measuring machine 12 that is operably connected to exchange data and control signals with a controlling computer system 14. The controlling computer system 14 is further operably connected to exchange data and control signals with a monitor or display 16, a printer 18, a joystick 22, a keyboard 24, and a mouse 26. The monitor or display 16 may display a user interface suitable for controlling and/or programming the operations of the machine vision inspection system 10. It will be appreciated that in various embodiments, a touchscreen tablet or the like may be substituted for and/or redundantly provide the functions of any or all of the computer system 14, the display 16, the joystick 22, a keyboard 24, and the mouse 26.

Those skilled in the art will appreciate that the controlling computer system 14 may generally consist of any computing system or device. Suitable computing systems or devices may include personal computers, server computers, minicomputers, mainframe computers, distributed computing environments that include any of the foregoing, and the like. Such computing systems or devices may include one or more processors that execute software to perform the functions described herein. Processors include programmable general-purpose or special-purpose microprocessors, programmable controllers, application specific integrated circuits (ASICs), programmable logic devices (PLDs), or the like, or a combination of such devices. Software may be stored in memory, such as random access memory (RAM), read-only memory (ROM), flash memory, or the like, or a combination of such components. Software may also be stored in one or more storage devices, such as magnetic or optical based disks, flash memory devices, or any other type of non-volatile storage medium for storing data. Software may include one or more program modules which include routines, programs, objects, components, data structures, and so on that perform particular tasks or implement particular abstract data types. In distributed computing environments, the functionality of the program modules may be combined or distributed across multiple computing systems or devices and accessed via service calls, either in a wired or wireless configuration.

The vision measuring machine 12 includes a moveable workpiece stage 32 and an optical imaging system 34 which may include a zoom lens or interchangeable lenses. The zoom lens or interchangeable lenses generally provide various magnifications for the images provided by the optical imaging system 34. The machine vision inspection system 10 is generally comparable to the QUICK VISION® series of vision systems and the QVPAK® software discussed above, and similar state-of-the-art commercially available precision machine vision inspection systems. The machine vision inspection system 10 is also described in commonly assigned U.S. Pat. Nos. 7,454,053, 7,324,682, 8,111,905, and 8,111,938, which are each incorporated herein by reference in their entireties.

Figure 2:
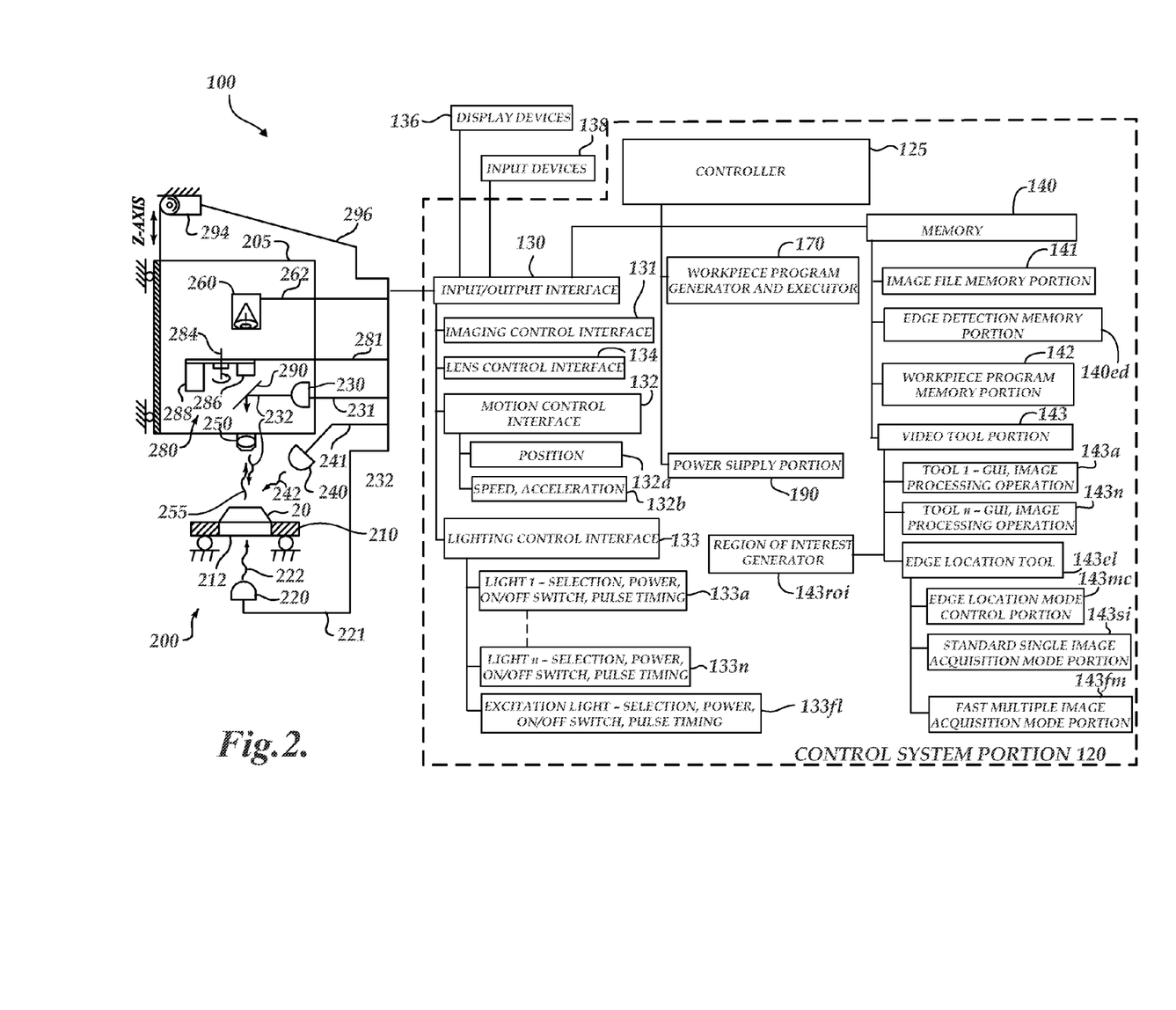
FIG. 2 is a block diagram of a control system portion and a vision components portion of a machine vision inspection system similar to that of FIG. 1, and including features described herein.

FIG. 2 is a block diagram of a control system portion 120 and a vision components portion 200 of a machine vision inspection system 100 similar to the machine vision inspection system of FIG. 1, and including features as described herein. As will be described in more detail below, the control system portion 120 is utilized to control the vision components portion 200. The vision components portion 200 includes an optical assembly portion 205, light sources 220, 230, and 240, and a workpiece stage 210 having a central transparent portion 212. The workpiece stage 210 is controllably movable along X and Y axes that lie in a plane that is generally parallel to the surface of the stage where a workpiece 20 may be positioned. The optical assembly portion 205 includes a camera system 260, an interchangeable objective lens 250, and may include a turret lens assembly 280 having lenses 286 and 288. Alternatively to the turret lens assembly, a fixed or manually interchangeable magnification-altering lens, or a zoom lens configuration, or the like, may be included.

The optical assembly portion 205 is controllably movable along a Z-axis that is generally orthogonal to the X and Y axes, by using a controllable motor 294 that drives an actuator to move the optical assembly portion 205 along the Z-axis to change the focus of the image of the workpiece 20. The controllable motor 294 is connected to the input/output interface 130 via a signal line 296.

A workpiece 20, or a tray or fixture holding a plurality of workpieces 20, which is to be imaged using the machine vision inspection system 100 is placed on the workpiece stage 210. The workpiece stage 210 may be controlled to move relative to the optical assembly portion 205, such that the interchangeable objective lens 250 moves between locations on a workpiece 20, and/or among a plurality of workpieces 20. One or more of a stage light 220, a coaxial light 230, and a surface light 240 (e.g. a ring light) may emit source light 222, 232, and/or 242, respectively, to illuminate the workpiece or workpieces 20. The light source 230 may emit light 232 along a path including a mirror 290. The source light is reflected or transmitted as workpiece light 255, and the workpiece light used for imaging passes through the interchangeable objective lens 250 and the turret lens assembly 280 and is gathered by the camera system 260. The image of the workpiece(s) 20, captured by the camera system 260, is output on a signal line 262 to the control system portion 120. The light sources 220, 230, and 240 may be connected to the control system portion 120 through signal lines or busses 221, 231, and 241, respectively. To alter the image magnification, the control system portion 120 may rotate the turret lens assembly 280 along axis 284 to select a turret lens, through a signal line or bus 281.

As shown in FIG. 2, in various exemplary embodiments, the control system portion 120 includes a controller 125, the input/output interface 130, a memory 140, a workpiece program generator and executor 170, and a power supply portion 190. Each of these components, as well as the additional components described below, may be interconnected by one or more data/control buses and/or application programming interfaces, or by direct connections between the various elements.

The input/output interface 130 includes an imaging control interface 131, a motion control interface 132, a lighting control interface 133, and a lens control interface 134. The motion control interface 132 may include a position control element 132a, and a speed/acceleration control element 132b although such elements may be merged and/or indistinguishable. The lighting control interface 133 includes lighting control elements 133a-133n, and 133fl which control, for example, the selection, power, on/off switch, and strobe pulse timing if applicable, for the various corresponding light sources of the machine vision inspection system 100.

The memory 140 may include an image file memory portion 141, an edge detection memory portion 140ed, a workpiece program memory portion 142 that may include one or more part programs, or the like, and a video tool portion 143. The video tool portion 143 includes video tool portion 143a and other video tool portions (e.g. 143n), which determine the GUI, image processing operation, etc., for each of the corresponding video tools, and a region of interest (ROI) generator 143roi that supports automatic, semi-automatic and/or manual operations that define various ROIs that are operable in various video tools included in the video tool portion 143.

In the context of this disclosure, and as known by one of ordinary skill in the art, the term video tool generally refers to a relatively complex set of automatic or programmed operations that a machine vision user can implement through a relatively simple user interface (e.g. a graphical user interface, editable parameter windows, menus, and the like), without creating the step-by-step sequence of operations included in the video tool or resorting to a generalized text-based programming language, or the like. For example, a video tool may include a complex pre-programmed set of image processing operations and computations which are applied and customized in a particular instance by adjusting a few variables or parameters that govern the operations and computations. In addition to the underlying operations and computations, the video tool comprises the user interface that allows the user to adjust those parameters for a particular instance of the video tool. For example, many machine vision video tools allow a user to configure a graphical region of interest (ROI)

indicator through simple "handle dragging" operations using a mouse, in order to define the location parameters of a subset of an image that is to be analyzed by the image procession operations of a particular instance of a video tool. It should be noted that the visible user interface features are sometimes referred to as the video tool, with the underlying operations being included implicitly.

In particular, in various embodiments according to this invention, the video tool portion 143 includes an edge location tool 143e1, which provides various operations and features related to edge location operations, as described in greater detail below. In common with many video tools, the edge location and multiple image acquisition subject matter of this disclosure includes both user interface features and underlying image processing operations, and the like, and the related features may be characterized as features of the edge location tool 143e1 included in the video tool portion 143. In one embodiment, the edge location tool 143e1 may include an edge location mode control portion 143mc, a standard single image acquisition mode portion 143si, and a fast multiple image acquisition mode portion 143fm. Briefly, the standard single image acquisition mode portion 143si may operate similarly to known edge location tools, for example, obtaining a single image, determining pixel intensity values and corresponding gradient magnitude values along a scan line across an edge in the image, and identifying the location of the edge as corresponding to a peak of the gradient magnitude. The fast multiple image acquisition mode portion 143fm operates based on the methods of the present invention. In contrast to the standard single image acquisition mode portion 143si, the fast multiple image acquisition mode portion 143fm utilizes a fast multiple image acquisition mode of a camera in conjunction with a simultaneous controlled motion of the stage and/or camera to obtain multiple images of an edge with a desired sub-pixel offset between the images. The image data is then combined and provides a resolution better than that allowed by the native resolution of a camera that acquires images in the machine vision inspection system. The edge location mode control portion 143mc may perform operations, as disclosed herein, to configure an edge location tool 143el, or tool modes, depending on which tool or mode is activated.

The camera system has a fast multiple image acquisition mode of operation such that a difference between the first and second times (t2−t1) at which sequential images may be captured is at most 50 microseconds, or at most 25, 10 or 5 microseconds in various embodiments, or even less if allowed by the camera system. In such embodiments, the fast multiple image acquisition mode of operation of the camera system allows (t2−t1) to be short enough to freeze vibrational effects present in the machine vision inspection system image (e.g. such that vibrational distortions are effectively constant during t2−t1), which is an important consideration with regard to the accuracy of the object reconstruction and measurement that is based on the combined image data that is provided by the two images acquired at the times t2 and t1. Furthermore, such a time (t2−t1) is short enough to allow the two corresponding images to exhibit a sub-pixel offset as desired, while allowing a relatively high motion speed during their acquisition. For example, with a magnification of 1, a sub-pixel offset of 2.5 microns may be obtained with a motion speed of 0.25 meters/second when (t2−t1) is 10 microseconds. It should be appreciated that conventional cameras in precision machine vision inspection systems are not able to provide this type of operation, typically providing frames rates of several milliseconds. However, some cameras are becoming available which may provide this type of operation. For example, when operated as described further below with reference to FIG. 7, the model AM-200CL from JAI Inc. (products and information available from JAI Inc., San Jose, Calif., USA) with a pixel pitch Dp=5.5 microns, may acquire two images with an interframe time of 5 microseconds, due to special signal processing features related to the camera detector pixel array. Such cameras, used in combination with the various other features and operations disclosed herein, provide a system that allows a desirable level of resolution and accuracy to be obtained by relatively unskilled users of a precision machine vision inspection system, while utilizing relatively inexpensive systems (e.g. existing motion control systems, in contrast to complex dithering components) and lower levels of magnification.

Alternative configurations are possible for the edge location tool 143el. For example, the standard single image acquisition mode portion 143si and the fast multiple image acquisition mode portion 143fm may include partitioned mode control functions such that a separate mode control portion 143mc may be omitted. Alternatively, the edge location tool 143el may provide one or more generic edge location tool elements, and the mode control portion 143mc may provide operations that govern the user interface and interrelationships of the generic edge location tool elements in a manner that depends on whether standard single image tool behavior, or fast multiple image with sub-pixel offset tool behavior, is desired. In such a case, the circuits, routines, or applications that provide the operations of the standard single image acquisition mode portion 143si and/or the fast multiple image acquisition mode portion 143fm, may be merged and/or indistinguishable. In certain implementations, the mode control portion 143mc may be utilized to implement a separate tool for the fast multiple image mode. More generally, this invention may be implemented in any now known or later-developed form that is operable in conjunction with the machine vision inspection system 100 to provide the features disclosed herein in relation to the fast multiple image with sub-pixel offset operations.

The signal lines or busses 221, 231 and 241 of the stage light 220, the coaxial lights 230 and 230', and the surface light 240, respectively, are all connected to the input/output interface 130. The signal line 262 from the camera system 260 and the signal line 296 from the controllable motor 294 are connected to the input/output interface 130. In addition to carrying image data, the signal line 262 may carry a signal from the controller 125 that initiates image acquisition.

One or more display devices 136 (e.g., the display 16 of FIG. 1) and one or more input devices 138 (e.g., the joystick 22, keyboard 24, and mouse 26 of FIG. 1) can also be connected to the input/output interface 130. The display devices 136 and input devices 138 can be used to display a user interface, which may include various graphical user interface (GUI) features that are usable to perform inspection operations, and/or to create and/or modify part programs, to view the images captured by the camera system 260, and/or to directly control the vision system components portion 200. The display devices 136 may display user interface features associated with the edge location video tool 143el.

In various exemplary embodiments, when a user utilizes the machine vision inspection system 100 to create a part program for the workpiece 20, the user generates part program instructions by operating the machine vision inspection system 100 in a learn mode to provide a desired image acquisition training sequence. For example a training sequence may comprise positioning a particular workpiece feature of a representative workpiece in the field of view (FOV), setting light levels, focusing or autofocusing, acquiring an image, and providing an inspection training sequence applied to the image (e.g. using an instance of one of the video tools on that workpiece feature). The learn mode operates such that the sequence(s) are captured or recorded and converted to corresponding part program instructions. These instructions, when the part program is executed, will cause the machine vision inspection system to reproduce the trained image acquisition and inspection operations to automatically inspect that particular workpiece feature (that is the corresponding feature in the corresponding location) on a run mode workpiece or workpieces which matches the representative workpiece used when creating the part program.

Figure 3:
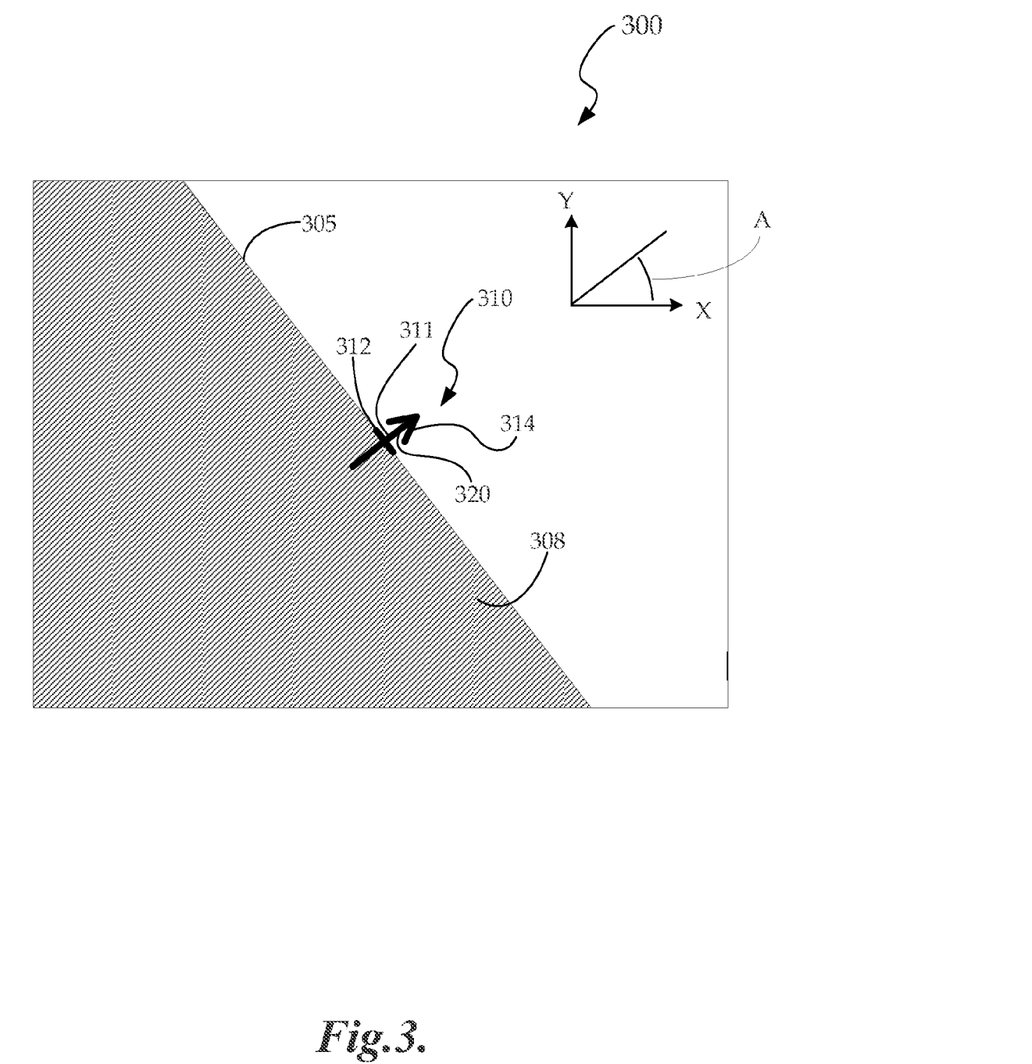
FIG. 3 is a diagram of an exemplary point tool overlaying an edge in an image.

FIG. 3 is a diagram of an exemplary point tool 310 overlaying an edge 305 at the boundary of a darker or shaded area 308 in an image 300 (e.g. on an image display device). The point tool 310, as well as other types of video tools for edge detection, are described in more detail in U.S. Pat. No. 7,567,713, which is hereby incorporated by reference in its entirety. In FIG. 3, the shaded area 308 is shown for purposes of illustration, to indicate relatively lower intensity pixels in the image 300. As will be described in more detail below, the point tool 310 may be configured for determining the location of an edge point in the image, and similar operations may underlie the operation of another type of tool (e.g. a box-type edge tool) that locates multiple edge points. A graphical user interface of the point tool 310 may include a body 311, an edge selector 312 and a polarity indicator arrowhead 314. The arrowhead 314 may generally point from light-to-dark, or dark-to-light, across an edge to enhance edge-finding reliability in certain situations, as explained in the incorporated references. In the illustration of FIG. 3, the body 311 obscures a nominal scan line 320 defined by, and nominally coinciding with, the body 311.

In operation, the user selects the point tool 310 (e.g. from a video tool bar at the edge of a display) and identifies an edge feature to be detected by placing the body 311 over the edge feature and the edge selector 312 as close as possible to the edge, at a desired location along the edge. The point tool body 311 may be oriented to define and indicate a desired scan line orientation across the edge, as indicated by the angle A in the illustrated x-y coordinate system in the upper right corner of FIG. 3. In FIG. 3, image pixels are arranged in rows along the x-coordinate direction and columns along the y-coordinate direction. Thus, the angle A indicates a nominal scan line orientation angle relative to the pixel rows in an image. The arrow 314 points along a reference direction or polarity to be associated with the edge detection (e.g. associated with whether the edge is detected as a rising edge, a falling edge, etc.) In operation, once the point tool 310 is completely configured, the instructions of an underlying edge point locating routine may be executed to perform operations that analyze intensity profile data points (e.g., pixel intensity data) associated with a scan line that nominally coincides with the body 311 of the point tool 310, and performs various operations to detect the edge location of the underlying feature. As will be described in more detail below with respect to FIG. 4, in various exemplary embodiments, the edge point locating routine of the point tool 310 may determine an edge location based on the magnitude of the gradient along an intensity profile associated with the scan line. It will be appreciated the scan line direction is not likely to coincide exactly with the image pixel row and/or column direction. In such a case, the image value at a "pixel" location along the scan line direction may be determined by interpolation based on the surrounding image pixels, according to various known methods. Computing interpolated image intensity along a desired line and/or direction based on previously obtained image data is taught for example in U.S. Pat. No. 7,567,713 to Ding, which is hereby incorporated herein by reference in its entirety.

The direction of the edge and scan line are related to another advantage of the systems and method disclosed herein, relative to the prior art. It will be appreciated that the relevant direction for the increased spatial sampling density (and the associated sub-pixel offset between combined images) outlined previously and described in greater detail below is nominally transverse (e.g. perpendicular) to the edge feature that is to be imaged and located with enhanced resolution. It will be appreciated that the systems and methods disclosed herein are particularly versatile in this regard (in contrast to previously known mechanical dithering methods that provided sub-pixel offsets only along a predetermined direction). In particular, a standard motion control system can provide a motion direction transverse to any edge, and the fast multiple image acquisition mode of operation of the camera can acquire images having the desired sub-pixel offset along that direction, which is most relevant to the purpose of the desired resolution improvement.

To summarize, in general, edge points are determined by various video tools, which may fit geometric forms to the edge points in order to measure corresponding underlying image features. In one conventional method of operating a video tool, depending on the type of tool (e.g. point/box/circle, etc.), one or more nominal scan lines are defined or generated within the ROI, according to defined tool parameters. For each nominal scan line, the tool determines or selects a set of intensity profile data point locations that approximate the nominal scan line. Intensity values associated with the data point locations are determined, to define the intensity profile associated with the nominal scan line. Then, in one embodiment, an edge detection algorithm analyzes gradients along the intensity profile to find the location along the intensity profile that corresponds to the maximum gradient magnitude, as described in more detail below with reference to FIG. 4, for example. The maximum gradient location along the intensity profile is used to determine the edge point location in the image that is associated with the nominal scan line.

Figure 4:
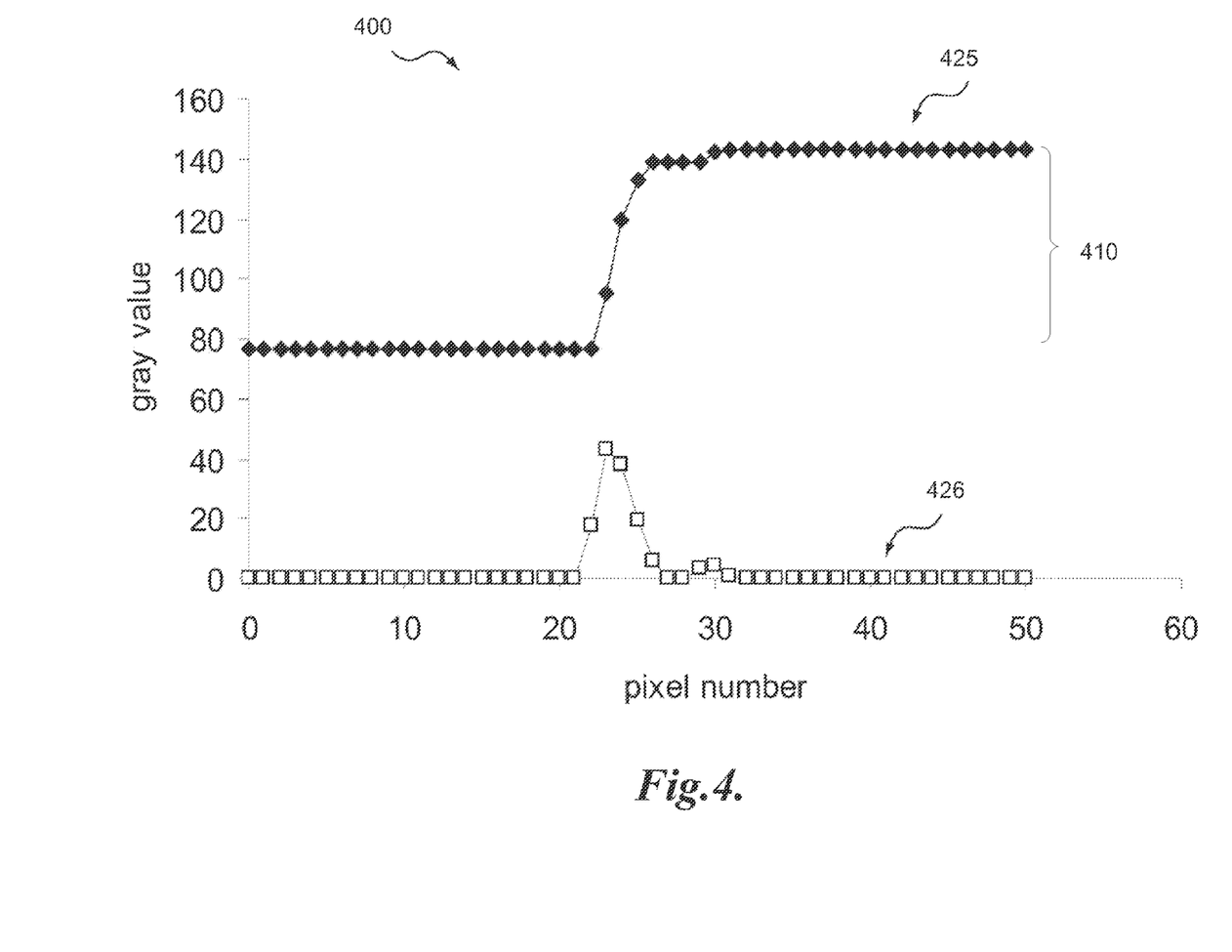
FIG. 4 is a diagram illustrating one exemplary method of determining an edge location based on a set of pixel intensity values.

FIG. 4 is a diagram of a graph 400 illustrating one exemplary method of determining an edge location based on an intensity profile 410. As shown in FIG. 4, the intensity profile 410 comprises a set of image pixel intensity (gray) values 425 corresponding to positions representing a scan line (e.g. such as the scan line 320 shown in FIG. 3). The data points or positions representing the scan line are labeled as "pixel numbers" from 0-50 along the horizontal axis. Beginning from data point 0, the image intensity values initially indicate a relatively darker region up to approximately data point 23, which is then followed by a relatively lighter region up to data point 50.

Gradient magnitude values 426 are derived from the intensity values 425 and are also shown in FIG. 4. Various conventional algorithms find the location along the horizontal axis that corresponds to a peak of the gradient magnitude, and identify that location as an edge location. If there are multiple gradient magnitude peaks, then the video tool edge selector and/or orientation indicator (e.g. edge selector 312 and/or polarity indicator 314 of the point tool 310) can help the algorithm identify the desired peak. In FIG. 4, the maximum gradient criterion (that is, the gradient peak) indicates that the edge is located at approximately data point 23. By using methods that may include curve fitting, centroid determination, or the like, a gradient magnitude peak may be located relatively precisely between the intensity profile data points, which generally supports sub-pixel measurement resolution and repeatability when determining the location of the corresponding edge in the image.

As will be described in more detail below with respect to FIGS. 5-8, in order to accurately determine the location of an edge in an image with sub-pixel measurement resolution, it is important that the image has a sufficient spatial sampling density. As a specific example, with reference to FIG. 4, there are approximately five data points (i.e., data points 22-26) located on the transition region for the edge 305 of FIG. 3. In certain implementations, this sampling density represents sufficient resolution for determining the location of the edge 305 with a desired sub-pixel level of accuracy. However, it will be appreciated that in an implementation where a lower level of magnification is utilized, the sampling density on the imaged object will be reduced, in that each pixel will correspond to a larger area of the object, and the centers of the areas will be spaced farther apart, which may average out or eliminate information related to fine structures and/or sharp edges on the object. With respect to the example of FIG. 4, in an implementation where only half the magnification is utilized (i.e., thus producing a larger field of view), the number of pixels corresponding to the edge transition will be reduced. For certain implementations, this lower sampling density may reduce the sub-pixel measurement resolution to an unacceptably low level, as will be described in more detail below with respect to FIG. 5. As will be described in more detail below with respect to FIGS. 6A-6C, the sampling density may effectively be increased through the utilization of multiple images. More specifically, sub-pixel offset image sampling operations may be utilized to acquire first and second images with a sub-pixel offset from one another. The data determined from the two images may then be combined to provide a composite image that has a higher spatial sampling density, to achieve a desired measurement resolution.

Figure 5:
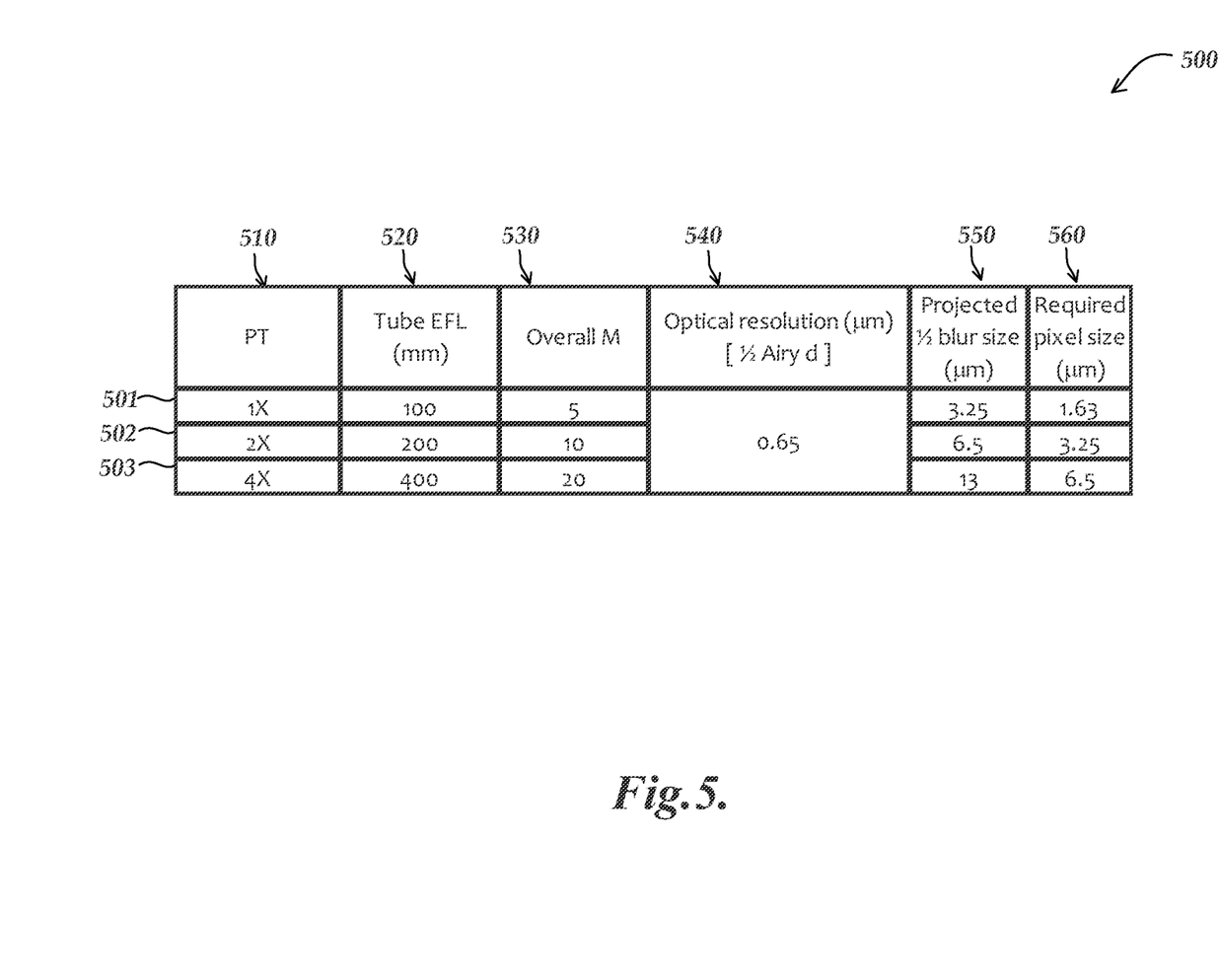
FIG. 5 is a diagram of a table illustrating the need for increased sampling of an edge at various magnifications.

FIG. 5 is a diagram of a table 500 illustrating the need for increased sampling of an edge at various magnifications. As shown in FIG. 5, the table 500 includes a PT column 510 showing a power turret lens magnification factor, a tube EFL column 520 showing a tube lens effective focal length, an overall magnification M column 530, a corresponding optical resolution column 540, a projected ½ blur size column 550 and a required sample separation column 560 showing a camera pixel pitch needed for sampling the ½ blur size at the Nyquist frequency, which insures that the camera pixel pitch is not the factor limiting the resolution of the image information. For a first row 501 of the table 500, the PT column 510 indicates a value of 1X, the tube EFL column 520 indicates a value of 100, the overall M column 530 indicates a value of 5, the optical resolution column 540 indicates a value of 0.65, the projected ½ blur size column 550 indicates a value of 3.25, and the required sample separation column 560 indicates a value of 1.63. For a second row 502, the PT column 510 indicates a value of 2X, the tube EFL column 520 indicates a value of 200, the overall M column 530 indicates a value of 10, the optical resolution column 540 indicates a value of 0.65, the projected ½ blur size column 550 indicates a value of 6.50, and the required sample separation column 560 indicates a value of 3.25. For a third row 503, the PT column 510 indicates a value of 4X, the tube EFL column 520 indicates a value of 400, the overall M column 530 indicates a value of 20, the optical resolution column 540 indicates a value of 0.65, the projected ½ blur size column 550 indicates a value of 13.00 and the required sample separation column 560 indicates a value of 6.50.

In general, the table 500 illustrates that for high microscope magnifications, an object may generally be over-sampled by a detector. The values of the table 500 represent those for a single objective lens with NA=0.42 (EFL=20 mm). As a specific example, certain existing cameras (e.g., a JAI AM-200CL—products and information available from JAI Inc., San Jose, Calif., USA) with a pixel pitch $D_p$=5.5 um would slightly over-sample the PT4X condition indicated in the row 503 (i.e., for which the required sample separation column 560 indicates a required value of 6.50 um or less, for which the pixel pitch of 5.50 um would meet this requirement.) In contrast, this pixel size would not meet the requirements indicated in the rows 501 and 502 for the PT1X and PT2X conditions, for which the required pixel pitch and/or sampling separation is no more than 1.63 um and 3.25 um, respectively, for which the pixel pitch of 5.50 um is too large. It will be appreciated that the various optical configurations used in a machine vision inspection system may be characterized in a manner analogous to that shown in the table 500, or the like, and the results stored for reference. Then, in certain embodiments, when a multiple image mode is included in an edge tool, the edge tools can evaluate the characterization of a current optical configuration to determine whether the image data resolution is limited by the optical resolution or the camera detector resolution (that is, the pixel pitch). If the camera detector resolution is the limiting factor, the user interface of the machine vision inspection system may offer the user the ability to select the multiple image mode of operation for an edge tool (which may be simply characterized as a "super resolution" selection, or the like), because that may potentially improve the measurement resolution of the edge tool. Alternatively, the machine vision inspection system may automatically select the multiple image mode of operation when the camera detector resolution is the limiting factor. This later "automatic" selection may further depend on a global setting that is set by the user, that allows or disallows the automatic selection within the context of an entire part program. For example, for workpieces that do not possess sharp edge transitions or very finely spaced edges, the camera detector resolution (that is, the pixel spacing) may still be adequate for sampling the spatial frequencies of the features on that workpiece, even if the camera detector resolution is the limiting factor in comparison to the resolution of the optical components.

While the PT value of 4X in the row 503 is shown to achieve a desired sampling density, for certain implementations the field of view may not adequately capture all of the desired edge features in a single image and/or may have higher distortion levels than desired and/or may be too expensive to implement, or a higher magnification lens may simply not be immediately available for some systems or users. In other words, in certain implementations the field of view and/or distortion levels and/or cost factors may dictate utilizing the PT values of 2X or 1X, even though a workpiece may contain features and/or edges that would desirably be imaged and measured with higher resolution. As will be described in more detail below with respect to FIGS. 6-8, by utilizing sub-pixel offset image sampling operations, data from multiple images may be acquired and combined so as to achieve a desired sampling density, repeatability, and/or accuracy even at relatively lower magnification levels that may be desirable for some of the reasons outlined above.

As a specific illustrative example, an image acquisition sequence may be performed using a camera that supports a fast multiple image acquisition mode of operation, e.g the previously referred to camera—the model AM-200CL from JAI Inc. (products and information available from JAI Inc., San Jose, Calif., USA) with a pixel pitch Dp=5.5 microns. The number of images per fast acquisition sequence for this specific type of camera is 2. With an approximately 2X undersampled condition (5.5:3.25), similar to that illustrated for row 502 of FIG. 5, a constant stage speed Vx can be prescribed to yield a Δx shift or offset at the object which results in a fraction 1/L of a pixel offset of the object at the camera when the magnification is M. For a ½ pixel offset L=2. Assuming a magnification of 10, then Δx=Dp/(L*M)=0.275 um. In one specific example, an interframe time Ti and light pulse time Tlp may be 6 microseconds and 4 microseconds, respectively. Therefore, an effective time difference Tdiff between the exposures (e.g. the time between latching the effective positions corresponding to the exposures, while in motion) may be taken as Tdiff=[0.5 Tlp+Ti+0.5 Tlp]=10 microseconds, where the factor(s) of ½ account for latching a position at the halfway point through the exposure period defined by the light pulse, to represent the average workpiece or image position due to motion during the exposure. So, the desired velocity Vx to give the desired offset in this example is Vx=(0.275 microns/10 microseconds)=27.5 mm/s. Thus, using these parameters, two images of the object may be acquired within 10 microseconds that have pixels displaced by approximately ½Dp; thereby increasing the spatial sample frequency of an edge relative to the pixel pitch in a single image by approximately 2X. Related discussion is also provided with reference to FIG. 7, below.

As another specific illustrative example, some cameras (e.g. those incorporating 2 CCD arrays) have a fast multiple image acquisition mode that can acquire 3 images within approximately 15 microseconds (e.g the model AD-081CL from JAI Inc.) with a pixel pitch Dp=4.65 microns. The number of images per fast acquisition sequence for this specific type of camera is 3. With an approximately 3X under-sampled condition (a desired/required sampling step of 1.63 microns, for example, similar to that illustrated for row 501 of FIG. 5), a constant stage speed Vx can be prescribed to yield a Δx shift or offset at the object which results in a fraction 1/L of a pixel offset of the object at the camera when the magnification is M. For a ⅓ pixel offset L=3. Assuming a magnification of 5, then Δx=Dp/(L*M)=0.31 um. In this specific example, an interframe time Ti & light pulse time Tlp may be 1.5 microseconds and 4 microseconds, respectively. Therefore, an effective time difference Tdiff between the first and second, and/or second and third, exposures (e.g. the time between latching the effective positions corresponding to two sequential exposures, while in motion) may be taken as Tdiff=[0.5 Tlp+Ti+0.5 Tlp]=5.5 microseconds, where the factor(s) of ½ account for latching a position at the halfway point through the exposure period defined by the light pulse, to represent the average workpiece or image position due to motion during the exposure. So, the desired velocity Vx to give the desired offsets between the 3 images in this example is Vx=(0.31 microns/5.5 microseconds)=56.4 mm/s.

Figure 6A:
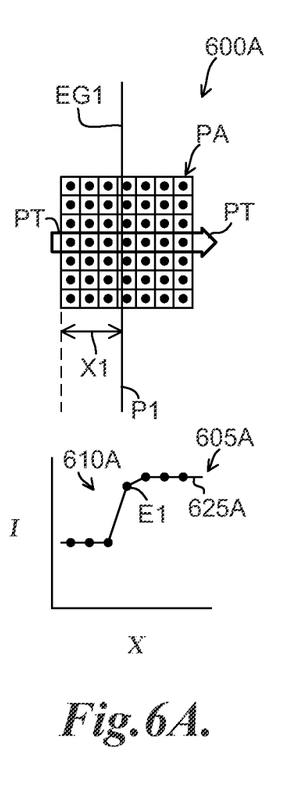
FIGS. 6A-6C are diagrams illustrating first and second images of an edge taken utilizing sub-pixel offset image sampling operations and combined data from the first and second images.
Figure 6B:
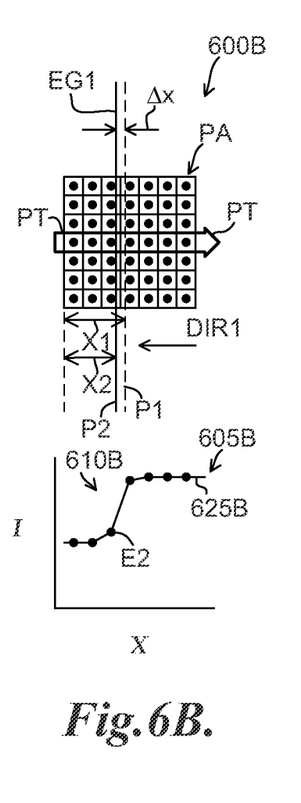
Figure 6C:
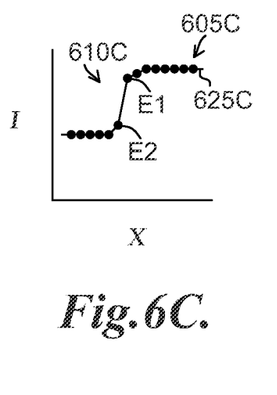

FIGS. 6A-6C are diagrams illustrating schematically represented first and second images 600A and 600B of an edge acquired utilizing sub-pixel offset image sampling operations and combined data 605C from the first and second images. As shown in FIG. 6A, the first image 600A illustrates a pixel array PA relative to an edge EG1 of a workpiece. The pixel array PA is shown to include seven rows and seven columns of pixels. A point tool PT (e.g., similar to the point tool 310 of FIG. 3) represents a scan line across the middle row of pixels of the pixel array PA. The edge EG1 is shown to be at a position P1, which is at a distance X1 from the left edge of the pixel array PA.

Below the image 600A, a graph 605A is shown which includes an intensity profile 610A (similar to the intensity profile 410 of FIG. 4.) The intensity profile 610A comprises a set of image pixel intensity (gray) values 625A corresponding to positions representing the scan line of the point tool PT. The data points from the scan line are illustrated as seven dots across the graph, one for each pixel. From left to right, the image intensity values initially indicate a relatively darker region for the first to the third pixels, which is then followed by a relatively lighter region, in particular for the fifth to the seventh pixels. The fourth pixel (i.e. the middle pixel) is labeled as having a pixel intensity value E1 which is shown to be between the high and low values of the other pixels, and represents a transitioning value for the edge EG1. It will be appreciated that the intensity profile 610A represents relatively limited sampling of the edge (e.g., in contrast to the intensity profile 410 of FIG. 4 for which multiple pixels are in the transitioning region for the edge.)

FIG. 6B illustrates an image 600B, in which the workpiece with the edge EG1 and the pixel array PA have been moved relative to one another by a sub-pixel offset equal to a distance ΔX. In other words, while the edge EG1 was located at a position P1 that was a distance X1 from the left edge of the pixel array PA in FIG. 6A, in FIG. 6B, the edge EG1 is shown to have been moved in a direction DIR1 so as to be located at a position P2 that is a distance X2 from the left edge of the pixel array PA. The difference between the distances X1 and X2 is the sub-pixel offset ΔX. It will be appreciated that in some embodiments, while the sub-pixel offset ΔX may sometimes be less than one pixel, in various other embodiments the sub-pixel offset ΔX may be more than one pixel, as long as it is not an integer number of pixels, so that the sampling density is increased as will be described in more detail below.

Below the image 600B, a graph 605B is shown which includes an intensity profile 610B. The intensity profile 610B includes data points corresponding to the seven pixel values corresponding to the scan line of the point tool PT. The third pixel is labeled as having a pixel intensity value E2 which represents a transitioning value for the edge EG1. Similar to the intensity profile 610A of FIG. 6A, the intensity profile 610B of FIG. 6B represents relatively limited sampling of the edge EG1.

FIG. 6C shows a graph 605C of an intensity profile 610C which illustrates combined data from the intensity profiles 610A and 610B of FIGS. 6A and 6B. As shown in FIG. 6C, fourteen pixel intensity values are illustrated, corresponding to the seven pixel intensity values from FIG. 6A and the seven pixel intensity values from FIG. 6B. The fourteen pixel intensity values of FIG. 6C thus represent a higher sampling density than that achieved by either of the individual images 600A or 600B. Thus, by utilizing multiple images with a sub-pixel shift of the object relative to the detector (e.g., as illustrated by images 600A and 600B) the sampling density of an edge may be increased.

It will be appreciated that the composite image data with the increased sampling density may also have the benefit of reducing the aliasing of edges that are closer together than twice the pixel pitch when magnified onto the camera, such as may be encountered when inspecting fine periodic structures such as gratings or IC masks, or the like. In certain applications, fine periodic features may be able to be resolved by the optics of a machine vision system, but may be spaced too closely together to be realistically imaged and/or measured when a camera with a limited pixel sampling density is utilized. By increasing the sampling density through the utilization of multiple images with sub-pixel offsets, the edges of the features with fine periodic patterns can be resolved and measured utilizing edge detection algorithms.

Figure 7:
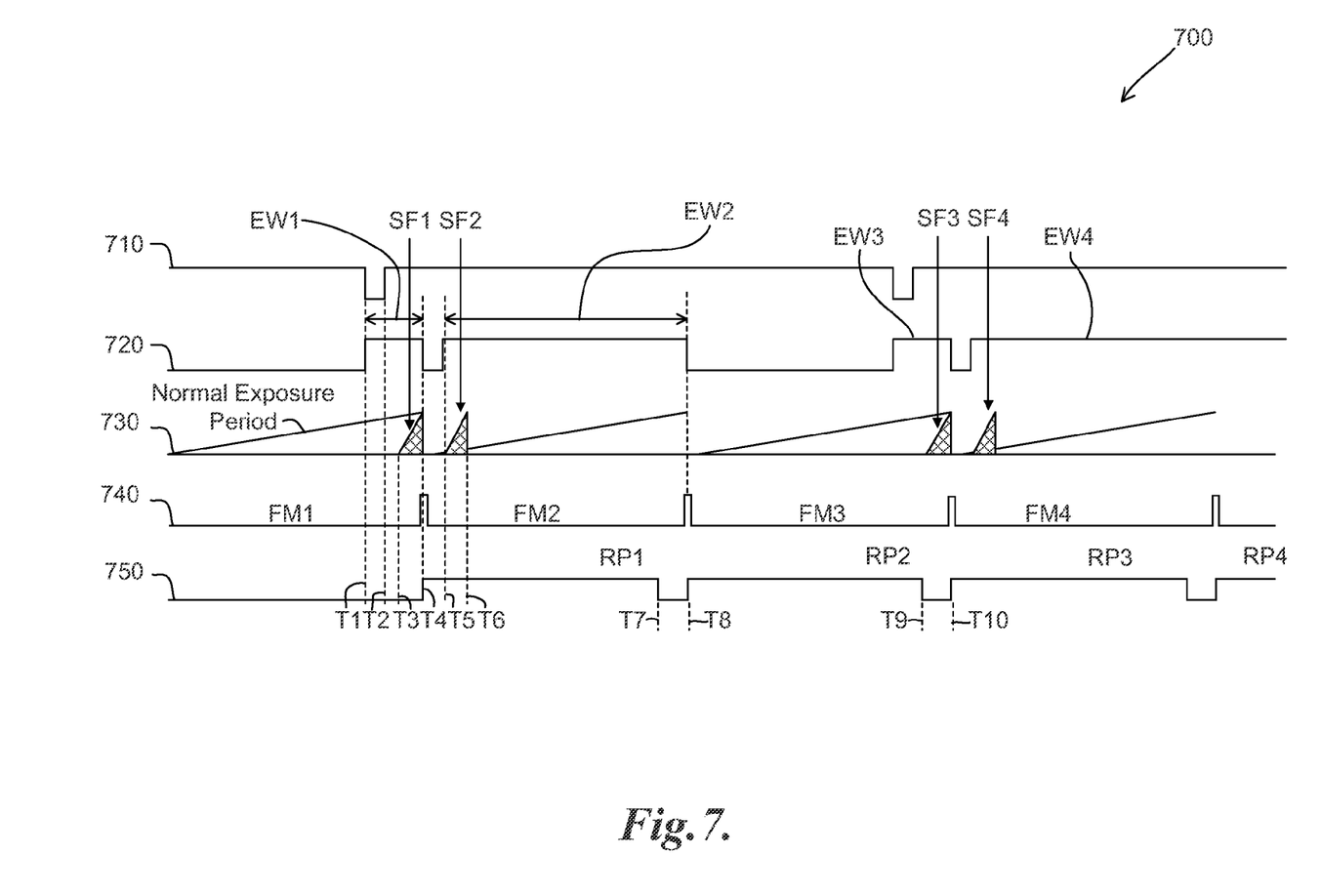
FIG. 7 is a timing diagram illustrating a sequence for acquiring the images of FIGS. 6A-6C.

FIG. 7 is a timing diagram 700 illustrating one exemplary sequence using a fast multiple image acquisition mode of operation of a camera that supports such a mode, for acquiring the images of FIGS. 6A and 6B. To achieve such operations, various commercially available cameras (e.g., JAI AM-200CL, JAI AD-081CL, PCO PixelFly, etc.) are available that provide a mode providing short interframing times of ~5 micro seconds and permit combining of two, three, or more rapidly acquired images (depending on the camera model). FIG. 7 illustrates an image timing sequence in one such camera (e.g., a JAI camera with 1-CCD that yields two images with a short interframe time.)

The timing diagram 700 includes a trigger signal line 710, an EEN signal line 720, an exposure signal line 730, a transfer gate signal line 740 and a readout signal line 750. At a time T1, the trigger signal line 710 is activated to go from high to low, and the EEN signal line 720 is correspondingly activated, thus beginning a first exposure window EW1 (e.g., with a timing of 4 us or 8 us, in various embodiments). At a time T2, the trigger signal line 710 returns to a high state. At a time T3, the exposure signal line 730 indicates an exposure period related to a first strobe flash SF1.

At a time T4, the EEN signal line 720 indicates the end of the first exposure window EW1, the exposure signal line 730 indicates the end of the exposure period related to the first strobe flash SF1, the transfer gate signal line 740 indicates the end of the first frame FM1 and the start of a second frame FM2. The triangular signal shape in the period (T4–T3) indicates that the exposure accumulates during that strobe period, starting at the time T3 and ending at the time T4. The second exposure starts at a time T5, after the interframe time (T5–T4). It will be appreciated that the interframe time (T5–T4) may be fixed or constrained by hardware or firmware characteristics in some embodiments of the fast multiple image acquisition mode. Thus, it should be appreciated that it may be desirable to know the timing of the end of the time T4 of the camera integration period (e.g. based on the trigger time of that integration period and its known duration) such that the strobe illumination may be set to expose the first image properly, and end approximately simultaneously with the end of the integration period at the time T4. This caused the effective exposure time of the first image to end just the interframe time away from the start of acquiring the second image, which makes the overall start and duration of the first image integration period largely irrelevant to the effective time delay between the first and second images. By way of example, and not by way of limitation, the time (T4–T3) may be on the order of 6 microseconds and the interframe time (T5–T4) may be on the order of 1.5-to-5 microseconds, in some embodiments and/or applications.

The readout signal line 750 indicates the beginning of a first readout period RP1 at the time T4. The first readout period RP1 corresponds to the readout of the image exposure accumulated on the signal line 730 between the times T3 and T4, corresponding to the first strobe flash SF1. At the time T5, the EEN signal line 720 indicates the beginning of a second exposure window EW2 (corresponding to one frame in certain implementations), and the exposure signal line 730 indicates an exposure period for a second strobe flash SF2. At a time T6, the exposure signal line 730 indicates that the exposure period for the second strobe flash SF2 ends.

At a time T7, the readout signal line 750 indicates the end of the first readout period RP1. (T7–T6) may be on the order of 16 milliseconds, in some embodiments and/or applications. At a time T8, the EEN signal line 720 indicates the end of the second exposure window EW2, the transfer gate signal line 740 indicates the end of the second frame FM2 and the beginning of a third frame FM3, and the readout signal line 750 indicates the beginning of a second readout period RP2.

The second readout period RP2 corresponds to the readout of the image exposure accumulated on the signal line 730 between the times T5 and T6, corresponding to the second strobe flash SF2. Beginning at a time T9, the fast multiple image acquisition mode of operation is ready for another cycle, if desired or needed, including the next set of strobe flashes SF3 and SF4, and the corresponding next set of readout periods RP3 and RP4.

Figure 8:
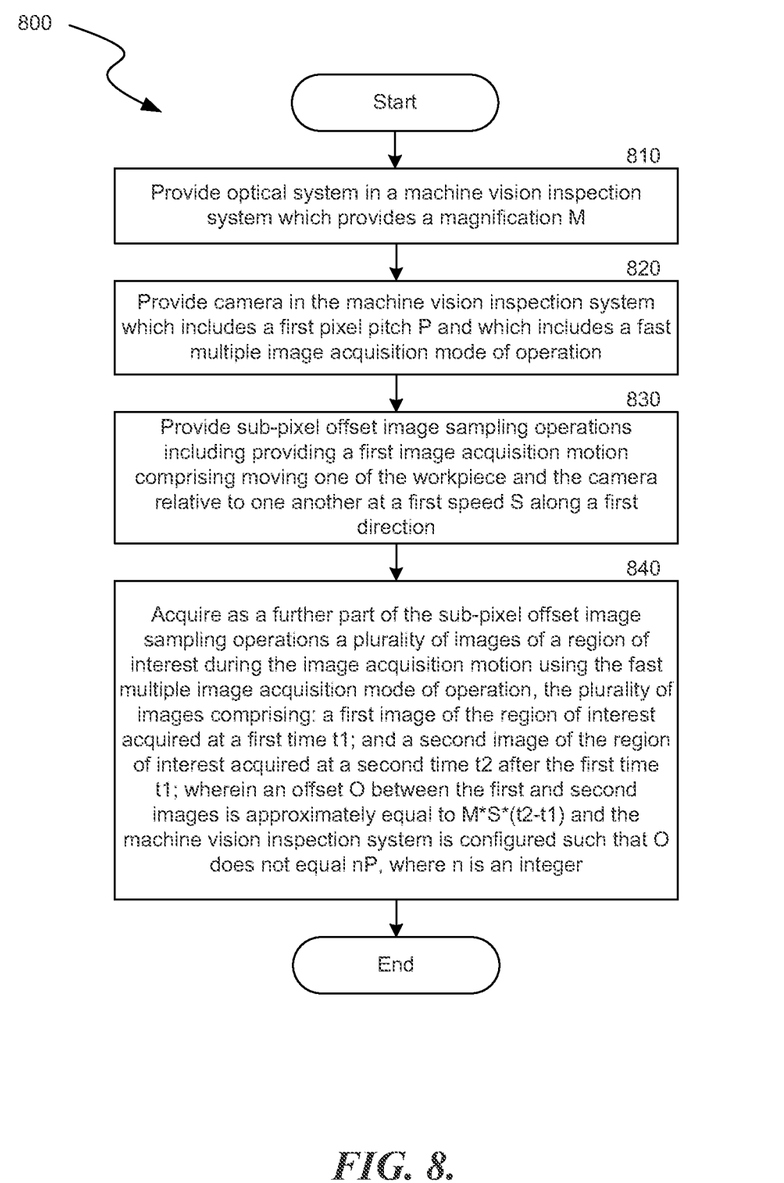
FIG. 8 is a flow diagram illustrating one exemplary embodiment of a routine for acquiring first and second images utilizing sub-pixel offset image sampling operations.

FIG. 8 is a flow diagram illustrating one exemplary embodiment of a routine 800 for acquiring first and second images utilizing a fast multiple image acquisition mode of operation to provide sub-pixel offset image sampling operations in a machine vision inspection system. At a block 810, an optical system is provided in a machine vision inspection system which provides a magnification M. At a block 820, a camera is provided in the machine vision inspection system which includes a first pixel pitch P and which includes a fast multiple image acquisition mode of operation. At a block 830, sub-pixel offset image sampling operations are provided including providing a first image acquisition motion comprising moving one of the workpiece and the camera relative to one another at a first speed S along a first direction. At a block 840, as a further part of the sub-pixel offset image sampling operations, a plurality of images are acquired of a region of interest during the image acquisition motion using the fast multiple image acquisition mode of operation. The plurality of images include at least a first image of the region of interest acquired at a first time t1, and a second image of the region of interest acquired at a second time t2 after the first time t1, with an offset O between the first and second images. The offset O is approximately equal to $M*S*(t2-t1)$, and the machine vision inspection system is configured such that O does not equal nP, where n is an integer.

From the foregoing, it will be appreciated that specific embodiments of the invention have been described herein for purposes of illustration, but that various modifications may be made without deviating from the scope of the invention. For example, those skilled in the art will appreciate that the depicted flow chart may be altered in a variety of ways. More specifically, the order of the steps may be re-arranged, steps may be performed in parallel, steps may be omitted, other steps may be included, etc. Accordingly, the invention is not limited except as by the appended claims.

I claim:

1. A method for acquiring a plurality of images in a machine vision inspection system to be utilized for performing measurement operations on a workpiece, the method comprising:

providing an optical system in the machine vision inspection system which provides a magnification M;

providing a camera in the machine vision inspection system which includes a first pixel pitch P and which includes a fast multiple image acquisition mode of operation;

providing sub-pixel offset image sampling operations comprising:

providing a first image acquisition motion comprising moving one of the workpiece and the camera relative to one another at a first speed S along a first direction;

acquiring a plurality of images of a region of interest during the image acquisition motion using the fast multiple image acquisition mode of operation, the plurality of images comprising:

a first image of the region of interest acquired at a first time t1; and a second image of the region of interest acquired at a second time t2 after the first time t1;

wherein an offset O between the first and second images is approximately equal to M*S*(t2−t1) and the machine vision inspection system is configured such that O does not equal nP, where n is an integer.

2. The method of claim 1, further including operating the machine vision system to process the plurality of images to remove the offset such that the workpiece is congruent in the images and combining the congruent image data to provide image data that has a resolution better than that allowed by the native resolution of the camera that acquires the plurality of images in the machine vision inspection system.

3. The method of claim 2, wherein the combining of the congruent image data is based on at least one of position latching; motion and timing; or correlation.

4. The method of claim 1, wherein the offset O falls within a range of (n+0.2)P<O<(n+0.8)P.

5. The method of claim 1, wherein the offset O falls within a range of (n+0.3)P<O<(n+0.7)P.

6. The method of claim 1, wherein the operations are included in a multiple image mode of an edge tool.

7. The method of claim 6, wherein the edge tool comprises a single image mode and the multiple image mode, the multiple image mode being utilized based on at least one of a magnification and a user selection.

8. The method of claim 6, wherein the edge tool comprises a single image mode and the multiple image mode, the image data from the first and second images taken during the multiple image mode being combined to increase the resolution to a level comparable to that obtainable for a single image taken with a higher magnification and a correspondingly smaller field of view during the single image mode.

9. The method of claim 1, wherein the first and second images include an edge of the workpiece in the region of interest.

10. The method of claim 9, wherein providing the first image acquisition motion comprises defining a motion direction that is transverse to an edge direction of the edge.

11. The method of claim 10, wherein the motion direction is defined by at least one of motion instructions in a part program during a run mode; a calculation; or a user definition during a learn mode.

12. The method of claim 10, wherein defining the motion direction comprises determining the edge direction and determining the motion direction transverse to the determined edge direction during a learn mode.

13. The method of claim 10, wherein defining the motion direction further comprises defining the motion direction in a part program.

14. The method of claim 9, wherein the edge location is determined based on the combined data of the first and second images.

15. The method of claim 14, wherein a composite image that is utilized for determining the edge location is made based on the combined data of the first and second images.

16. The method of claim 15, wherein the composite image is displayed during a learn mode.

17. The method of claim 1, wherein the system is configured during a learn mode, and the configuration is recorded in a part program.

18. The method of claim 1, wherein the image acquisition motion is provided utilizing at least a first macroscopic motion axis of the machine vision inspection system.

19. The method of claim 1, wherein (t2−t1) is at most 50 microseconds.

20. The method of claim 1, wherein (t2−t1) is at most 5 microseconds.

21. The method of claim 1, further comprising utilizing strobe lighting with timing in relation to the first time t1 and the second time t2 for acquiring the first and second images.

22. The method of claim 1, wherein the first pixel pitch P is at least one of a column-direction pixel pitch Py or a row-direction pixel pitch Px, and the offset O comprises a component Ox along a column direction of the camera having the pixel pitch Px and a component Oy along a row direction of the camera having the pixel pitch Py.

23. The method of claim 22, wherein the first image acquisition motion and an image timing in the fast multiple image acquisition mode of operation are configured such that at least one of the offset components comprises a non integer number K times the corresponding pixel pitch.

24. The method of claim 23, wherein the non integer number K falls within a range of (n+0.2)<K<(n+0.8), where n is an integer.

25. The method of claim 23, wherein the non integer number K falls within a range of (n+0.3)<K<(n+0.7), where n is an integer.

26. The method of claim 1, wherein the first and second images include a plurality of edges of the workpiece in the region of interest, and the first image acquisition motion comprises defining a motion direction that is transverse to an edge direction of an edge, and if a determination is made that a plurality of edge tools are being utilized within the region of interest with respect to the plurality of edges, then an option is provided to a user to assist with the determination of the motion direction.

27. The method of claim 1, wherein the first and second images include an edge of the workpiece in the region of interest, and the first image acquisition motion comprises defining a motion direction that is transverse to an edge direction of the edge, wherein a learn mode comprises:
   measuring the edge;
   determining an angle of the edge;
   setting the motion direction to an angle equal to the angle of the edge plus 90 degrees; and
   computing two waypoints based on the motion direction and tool location parameters.

28. The method of claim 27, wherein the first and second images include a plurality of edges of the workpiece in the region of interest, and if a determination is made that a plurality of edge tools are being utilized within the region of interest with respect to the plurality of edges, then the learn mode further comprises:
   determining the angles of the plurality of edges; and
   determining if a single motion direction can be determined that is within a specified range of degrees from perpendicular with respect to each of the angles of the plurality of edges, and if so, using the determined motion direction, and if not, adding at least a second motion direction for obtaining at least a third image.

29. A machine vision inspection system for acquiring a plurality of images to be utilized for performing measurement operations on a workpiece, the machine vision inspection system comprising:
   an optical system which provides a magnification M;
   a camera which includes a first pixel pitch P and which includes a fast multiple image acquisition mode of operation;
   a memory for storing programmed instructions;
   a processor configured to execute the programmed instructions to perform operations including:
      providing sub-pixel offset image sampling operations comprising:

providing a first image acquisition motion comprising moving one of the workpiece and the camera relative to one another at a first speed S along a first direction;

acquiring a plurality of images of a region of interest during the image acquisition motion using the fast multiple image acquisition mode of operation, the plurality of images comprising:

a first image of the region of interest acquired at a first time t1; and a second image of the region of interest acquired at a second time t2 after the first time t1;

wherein an offset O between the first and second images is approximately equal to $M*S*(t2-t1)$ and the machine vision inspection system is configured such that O does not equal nP, where n is an integer.

30. The machine vision inspection system of claim 29, wherein the operations further include removing the offset such that the workpiece is congruent in the images and combining the congruent image data to provide image data that has a resolution better than that allowed by the native resolution of a camera that acquires images in the machine vision inspection system.

31. A non-transitory computer readable storage medium with instructions stored thereon that are executable by a processor in a machine vision inspection system to perform operations of:

providing sub-pixel offset image sampling operations utilizing an optical system of the machine vision inspection system which provides a magnification M, the sub-pixel offset image sampling operations comprising:

providing a first image acquisition motion comprising moving one of a workpiece and a camera relative to one another at a first speed S along a first direction, the camera having a first pixel pitch P and including a fast multiple image acquisition mode of operation;

acquiring a plurality of images of a region of interest during the image acquisition motion using the fast multiple image acquisition mode of operation, the plurality of images comprising:

a first image of the region of interest acquired at a first time t1; and a second image of the region of interest acquired at a second time t2 after the first time t1;

wherein an offset O between the first and second images is approximately equal to $M*S*(t2-t1)$ and the machine vision inspection system is configured such that O does not equal nP, where n is an integer.

32. The non-transitory computer readable storage medium of claim 31, wherein the operations further include removing the offset such that the workpiece is congruent in the images and combining the congruent image data to provide image data that has a resolution better than that allowed by the native resolution of a camera that acquires images in the machine vision inspection system.

* * * * *